United States Patent
Hong et al.

(10) Patent No.: US 12,343,161 B2
(45) Date of Patent: Jul. 1, 2025

(54) METHOD AND APPARATUS FOR ANALYZING DEMENTIA SEVERITY USING FRONTAL LOBE SKIN IMAGE

(71) Applicant: Research & Business Foundation SUNGKYUNKWAN UNIVERSITY, Suwon-si (KR)

(72) Inventors: Kwang Seok Hong, Suwon-si (KR); Jin Soo Park, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 649 days.

(21) Appl. No.: 17/678,649

(22) Filed: Feb. 23, 2022

(65) Prior Publication Data

US 2022/0265211 A1 Aug. 25, 2022

(30) Foreign Application Priority Data

Feb. 24, 2021 (KR) .................. 10-2021-0025098

(51) Int. Cl.
| | |
|---|---|
| A61B 5/00 | (2006.01) |
| G06T 7/00 | (2017.01) |
| G06T 7/90 | (2017.01) |
| G16H 30/40 | (2018.01) |
| G16H 50/30 | (2018.01) |

(52) U.S. Cl.
CPC .......... *A61B 5/4842* (2013.01); *G06T 7/0012* (2013.01); *G06T 7/90* (2017.01); *G16H 30/40* (2018.01); *G16H 50/30* (2018.01); *G06T 2207/30088* (2013.01)

(58) Field of Classification Search
CPC ... A61B 5/4088; A61B 5/4064; A61B 5/4082; A61B 5/165; A61B 5/0059; A61B 5/168; A61B 5/372; A61B 5/6814; A61B 5/0042; A61B 5/72; A61B 5/374; A61B 5/4076; A61B 5/369; A61B 5/0064; A61B 5/4842; A61B 2576/026; A61B 8/0808; A61B 6/541; A61B 6/501; G16H 50/20; G16H 10/60; G16H 50/30; G16H 30/20; G16H 30/40; A61N 1/36082; G06V 40/171; G06V 40/174; G06V 40/15; G06T 7/0012; G06T 2207/30016; G06T 2207/30088; G06T 2207/30201; G06T 2207/20056; G06T 7/90

See application file for complete search history.

(56) References Cited

U.S. PATENT DOCUMENTS

| | | | |
|---|---|---|---|
| 10,884,090 B2 * | 1/2021 | Chance | A61B 5/4088 |
| 2017/0258390 A1 * | 9/2017 | Howard | A61B 5/4803 |
| 2018/0125409 A1 * | 5/2018 | Tahara | A61B 5/378 |
| 2021/0366613 A1 * | 11/2021 | Schler | G06V 10/764 |

* cited by examiner

*Primary Examiner* — Aaron W Carter
*Assistant Examiner* — Courtney Joan Nelson
(74) *Attorney, Agent, or Firm* — NSIP Law

(57) ABSTRACT

A method for analyzing dementia severity, may comprise calculating color data from skin regions of interest of a frontal lobe region; calculating frequency values corresponding to a frequency band of a dementia-related biosignal based on the calculated color data; and analyzing dementia severity using the calculated frequency values.

20 Claims, 13 Drawing Sheets

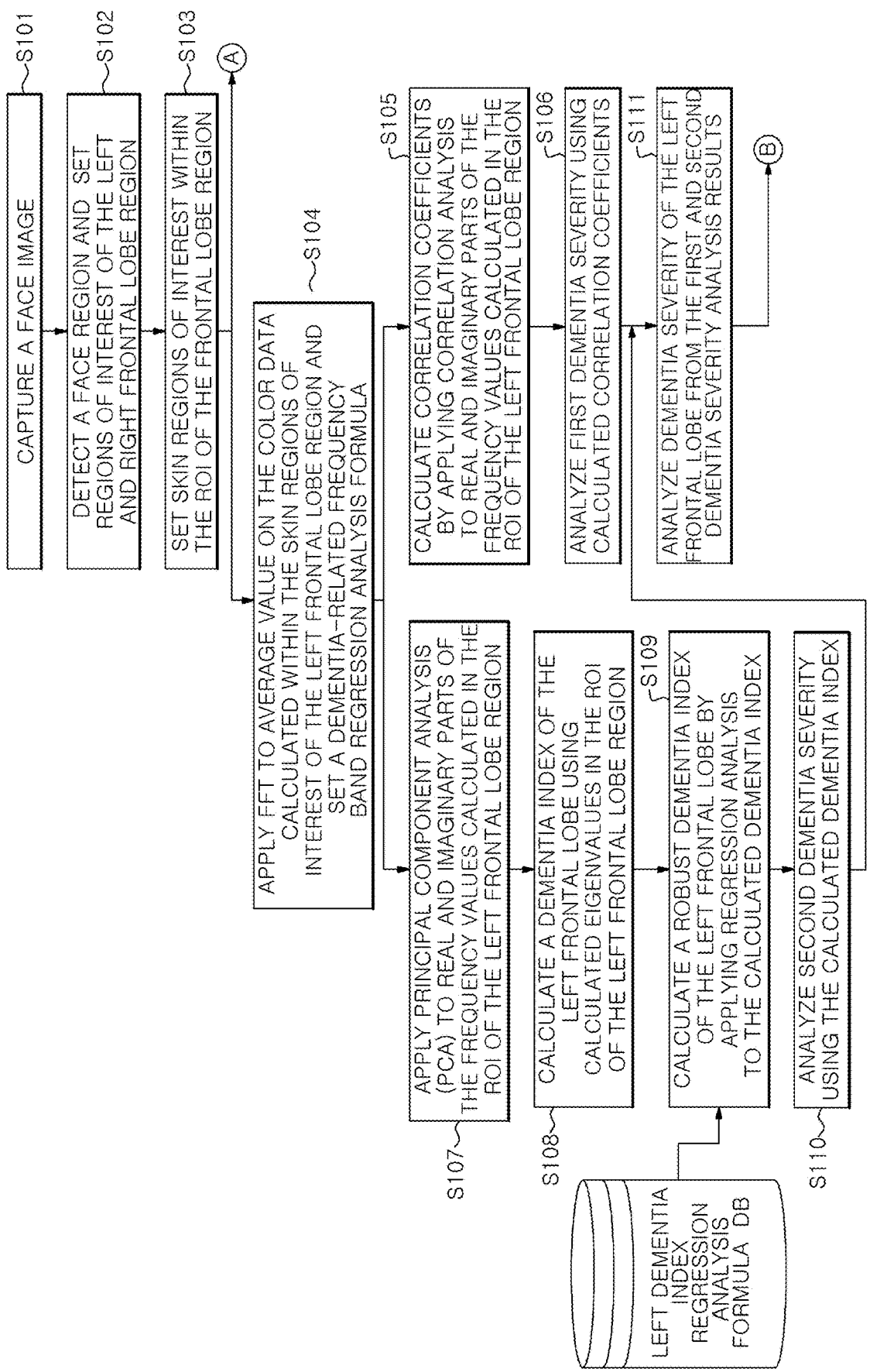

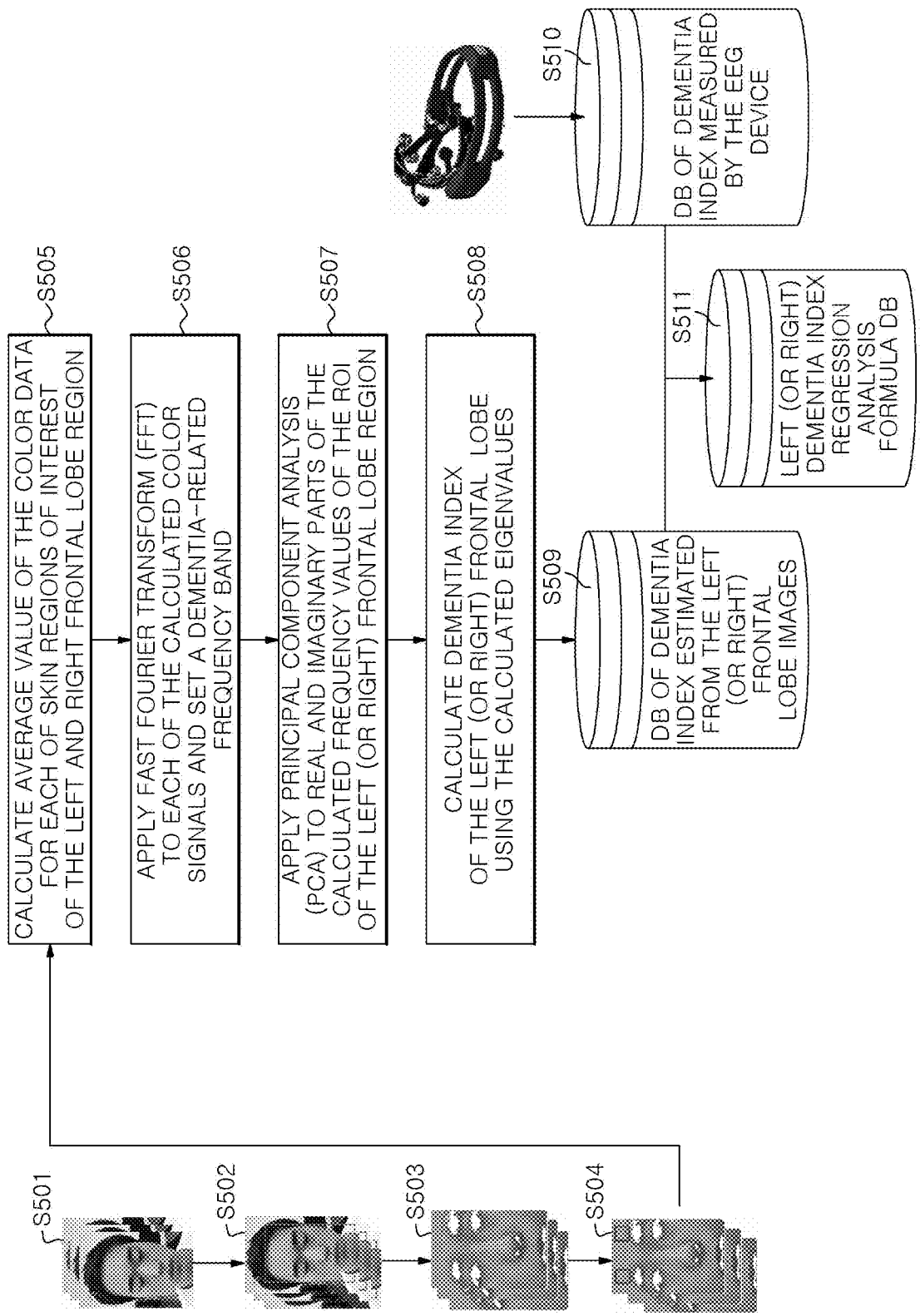

METHOD AND APPARATUS FOR ANALYZING DEMENTIA SEVERITY USING FRONTAL LOBE SKIN IMAGE

CROSS REFERENCE TO RELATED APPLICATIONS

This application claims the benefit under 35 USC § 119(a) of Korean Patent Application No. 10-2021-0025098, filed on Feb. 24, 2021.

TECHNICAL FIELD

The present disclosure relates to a method and apparatus for analyzing dementia severity using frontal lobe skin images.

BACKGROUND

The medical definition of dementia is "acquired multiple disorders that interfere with daily life by causing cognitive impairment in memory, linguistic ability, orientation, judgment, and competency due to degenerative brain disease or cerebrovascular disease." It is crucial to detect, prevent, and treat dementia as early as possible. Early symptoms of dementia should be suspected; otherwise, the symptoms may be readily misunderstood as natural symptoms of aging, which only delay diagnosis. Also, diseases such as Alzheimer's and vascular dementia start with memory loss as brain cells die one by one and eventually make people lose the ability to take care of themselves with impairment in linguistic ability, sense of orientation, and judgment. Dementia is caused by atherosclerosis of brain blood vessels or repeated cerebral strokes due to diabetes or high blood pressure, which may be avoided by early prevention. If dementia is detected at an early stage, further progression may be prevented.

First, a dementia screening test based on a dementia screening questionnaire will be described. The dementia severity analysis was developed to analyze and prevent or manage a subject's dementia state in the form of a dementia screening questionnaire or counseling by a professional counselor. The effectiveness of this technique relies on the professional counselor's subjective judgment. In the case of severe cognitive impairment, a mismatch is often observed between the questionnaire and symptom severity; furthermore, the technique may not be directly applied to dementia patients.

Second, dementia screening tests based on brain nuclear magnetic resonance imaging (Brain NMRI), brain positron emission tomography (PET), genetic analysis, or EEG signal measuring instruments will be described. These dementia screening tests require an expensive process involving magnetic resonance imaging (MRI) or positron emission tomography (PET) and take about 2 hours or more to complete. Recent studies on a new dementia screening method based on an EEG measurement device attempt to replace the existing tests. The recent studies on a new dementia test pay attention to a dementia diagnosis method for dementia screening based on EEG signals, which shortens the test time and lowers the cost. The dementia diagnosis method has the advantage that it is harmless by not causing pain to the human body and measures EEG signals from electrodes attached to the forehead using a prefrontal EEG measurement device. However, when dementia is tested based on the analysis of EEG signals, a test individual has to attach contact pads to the forehead, which may burden the individual to attach the pads.

SUMMARY

Therefore, to alleviate the problems above and replace existing dementia severity measurement devices, a method, which captures non-contact skin images of the left and right frontal lobes using an ordinary camera owned by an individual or an infrared camera without wearing an additional hardware module, estimates dementia severity using the captured images, and analyzes the dementia severity based on the estimation, is needed.

To this end, the embodiments of the present disclosure provide a method and an apparatus for analyzing dementia severity using images capturing skin regions of interest of the left and right frontal lobes rather than the existing test methods based on brain nuclear magnetic resonance imaging (MRI), brain positron emission tomography (PET), or genetic analysis.

However, the technical problem to be solved by the present disclosure is not limited to the above but may be extended to other various problems belonging to the scope not departing from the technical principles and domain of the present disclosure.

In accordance with an aspect of the present disclosure, there is provided a method for analyzing dementia severity, the method comprising: calculating color data from skin regions of interest of a frontal lobe region; calculating frequency values corresponding to a frequency band of a dementia-related biosignal based on the calculated color data; and analyzing dementia severity using the calculated frequency values.

The analyzing dementia severity may include analyzing a first dementia severity for detected skin regions of interest of a left frontal lobe region of the frontal lobe region using the frequency values calculated by applying Fast Fourier Transform (FFT) to an average value of the color data calculated within the skin regions of interest, analyzing a second dementia severity using the calculated frequency values, and analyzing an improved dementia severity of the left frontal lobe based on results of analyzing the first and the second dementia severity.

The analyzing dementia severity may include calculating correlation coefficients by applying correlation analysis to real and imaginary parts of the frequency values calculated by applying FFT to the average value of the color data calculated within the skin regions of interest of the left frontal lobe region and analyzing the first dementia severity using the calculated correlation coefficients.

The analyzing dementia severity may include calculating a dementia index of the left frontal lobe by applying principal component analysis to the frequency values calculated by applying FFT to the average value of the color data calculated within the skin regions of interest of the left frontal lobe region and analyzing the second dementia severity using the calculated dementia index of the left frontal lobe.

The analyzing dementia severity may include calculating eigenvalues by applying principal component analysis to real and imaginary parts of the frequency values calculated by applying FFT to the average value of the color data calculated within the skin regions of interest of the left frontal lobe region and calculating the dementia index of the left frontal lobe using the calculated eigenvalues.

The analyzing dementia severity may include calculating a robust dementia index of the left frontal lobe by applying the calculated dementia index of the left frontal lobe to a regression analysis formula and analyzing the second dementia severity using the robust dementia index of the left frontal lobe.

The analyzing dementia severity may include analyzing a third dementia severity using the frequency values calculated by applying FFT to an average value of the color data calculated within the skin regions of interest of a right frontal lobe region of the frontal lobe region, analyzing a fourth dementia severity using the calculated frequency values, and analyzing an improved dementia severity of a right frontal lobe based on results of analyzing the third and the fourth dementia severity.

The analyzing dementia severity may include calculating correlation coefficients by applying correlation analysis to real and imaginary parts of the frequency values calculated by applying FFT to the average value of the color data calculated within the skin regions of interest of the right frontal lobe region and analyzing the third dementia severity using the calculated correlation coefficients.

The analyzing dementia severity may include calculating a dementia index of the right frontal lobe by applying principal component analysis to the frequency values calculated by applying FFT to the average value of the color data calculated within the skin regions of interest of the right frontal lobe region and analyzing the fourth dementia severity using the calculated dementia index of the right frontal lobe.

The analyzing dementia severity may include calculating eigenvalues by applying principal component analysis to real and imaginary parts of the frequency values calculated by applying FFT to the average value of the color data calculated within the skin regions of interest of the right frontal lobe region and calculating a dementia index of the right frontal lobe using the calculated eigenvalues.

The analyzing dementia severity may include calculating a robust dementia index of the left frontal lobe by applying the calculated dementia index of the left frontal lobe to a regression analysis formula and analyzing the second dementia severity using the robust dementia index of the left frontal lobe.

The method further comprises calculating biosignal based on the calculated color data and providing a biosignal-based customized sound source corresponding to a dementia severity targeted by the user based on the analyzed dementia severity.

The method further comprises calculating biosignal using the calculated color data and providing information on a biosignal-based pulse wave or respiration adjustment training corresponding to a dementia severity targeted by the user based on the analyzed dementia severity.

In accordance with another aspect of the present disclosure, there is provided an apparatus for analyzing dementia severity, the apparatus comprising: an image acquisition module capturing a face image; a memory storing one or more programs related to a dementia severity analysis operation using frontal lobe skin images; and a processor executing the stored one or more programs, wherein the processor is configured to: calculate color data from skin regions of interest of a frontal lobe region extracted within the face image; calculate frequency values corresponding to a frequency band of a dementia-related biosignal based on the calculated color data; and analyze dementia severity using the calculated frequency values.

The processor is configured to analyze a first dementia severity for extracted skin regions of interest of a left frontal lobe region of the frontal lobe region using the frequency values calculated by applying Fast Fourier Transform (FFT) to an average value of the color data calculated within the skin regions of interest, analyze a second dementia severity using the calculated frequency values, and analyze a improved dementia severity of the left frontal lobe based on results of analyzing the first and the second dementia severity.

The processor is configured to calculate correlation coefficients by applying correlation analysis to real and imaginary parts of the frequency values calculated by applying FFT to the average value of the color data calculated within the skin regions of interest of the left frontal lobe region and analyze the first dementia severity using the calculated correlation coefficients.

The processor is configured to analyze a third dementia severity for extracted skin regions of interest of a right frontal lobe region of the frontal lobe region using the frequency values calculated by applying Fast Fourier Transform (FFT) to an average value of the color data calculated within the skin regions of interest of the right frontal lobe region, analyze a fourth dementia severity using the checked frequency values, and analyze an improved dementia severity of the right frontal lobe based on results of analyzing the third and the fourth dementia severity.

The apparatus further comprises an interface module configured to provide a dementia management interface to a user.

The processor is configured to calculate biosignal based on the calculated color data and provide a biosignal-based customized sound source corresponding to a dementia severity targeted by the user based on the analyzed dementia severity for the user through the interface module.

The processor is configured to calculate biosignal based on the calculated color data and provide information on a biosignal-based pulse wave or respiration adjustment training corresponding to dementia severity targeted by the user based on the analyzed dementia severity for the user through the interface module.

In accordance with another aspect of the present disclosure, there is provided a non-transitory computer-readable storage medium storing instructions instructing the processor to execute a method, the method comprising: calculating color data from skin regions of interest of a frontal lobe region; calculating frequency values corresponding to a frequency band of a dementia-related biosignal based on the calculated color data; and analyzing dementia severity using the calculated frequency values.

The present disclosure may provide the following effects. However, since it is not meant that a specific embodiment has to provide all of or only the following effects, the technical scope of the present disclosure should not be regarded as being limited by the specific embodiment.

The embodiments of the present disclosure may reduce the measurement time compared with the existing test methods based on brain nuclear magnetic resonance imaging (MRI), brain positron emission tomography (PET), genetic analysis, a dementia screening questionnaire, or an EEG measurement device. Also, the embodiments of the present disclosure may conveniently analyze the dementia severity using images captured through a portable device owned by a test individual. Also, a method and an apparatus for analyzing dementia severity according to an embodiment of the present disclosure allows an individual to check the individual's dementia state conveniently anytime and anywhere. Therefore, patients may be managed independently of time or place.

BRIEF DESCRIPTION OF THE DRAWINGS

FIGS. 1A and 1B illustrate a process of measuring a dementia index using skin images of the left and right frontal lobes and analyzing dementia severity according to one embodiment of the present disclosure.

FIG. 7 illustrates a process of calculating an improved dementia index regression line (or curve) formula and storing the calculated formula in the "left (or right) dementia index regression analysis formula DB" according to one embodiment of the present disclosure.

DETAILED DESCRIPTION

Figure 1B:
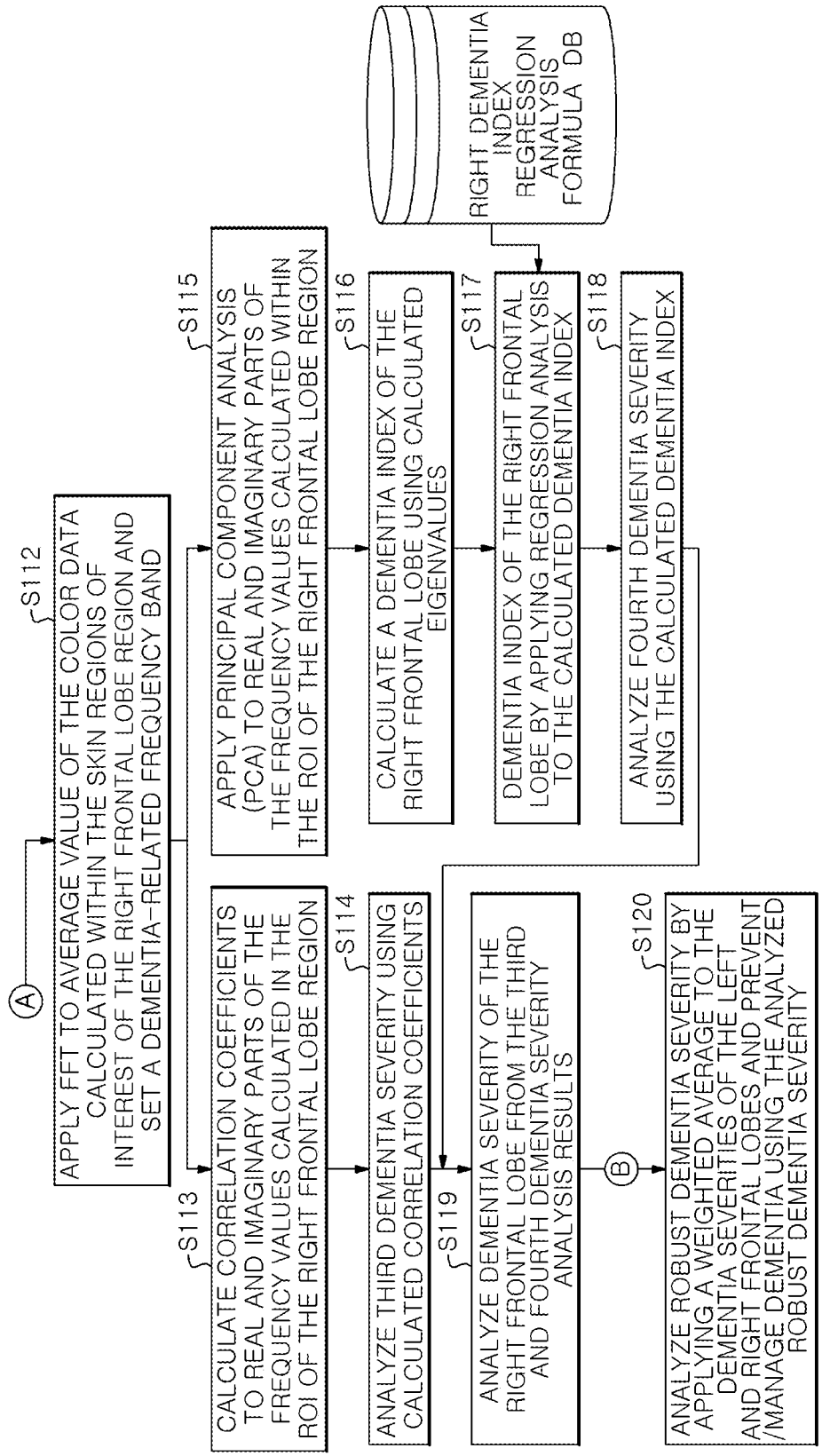

Since the present disclosure may be modified in various ways and may provide various embodiments, specific embodiments will be depicted in the appended drawings and described in detail with reference to the drawings. However, it should be understood that the specific embodiments are not intended to limit the gist of the present disclosure to the specific embodiments; rather, it should be understood that the specific embodiments include all of the modifications, equivalents, and/or alternatives of the embodiments of the present disclosure. Also, in describing an embodiment of the present disclosure, if it is determined that a detailed description of a related art incorporated herein unnecessarily obscures the gist of the embodiment, the detailed description thereof will be omitted.

Terms such as "first" and "second" may be used to describe various constituting elements, but the constituting elements should not be limited by the terms. The terms are introduced to distinguish one element from the others.

Terms used in one embodiment of the present disclosure are intended only for describing a specific embodiment and are not intended to limit the technical scope of the present disclosure. Terms used in one embodiment of the present disclosure have been selected as much as possible from general terms relevant to the functions of the present disclosure and currently in wide use; however, the selection of terms may vary depending on the intention of those persons skilled in the corresponding field, precedents, or emergence of new technologies. Also, in a particular case, some terms may be selected arbitrarily by the applicant, and in this case, detailed definitions of the terms will be provided in the corresponding description of the present disclosure. Therefore, the terms used in one embodiment of the present disclosure should be defined not simply by their apparent name but based on their meaning and context throughout the present disclosure.

A singular expression should be understood to indicate a plural expression unless otherwise explicitly stated. The term "include" or "have" in one embodiment of the present disclosure is used to indicate existence of an embodied feature, number, step, operation, constituting element, component, or a combination thereof; and should not be understood to preclude the existence or possibility of adding one or more other features, numbers, steps, operations, constituting elements, components, or a combination thereof.

In what follows, embodiments of the present disclosure will be described in detail with reference to appended drawings. In describing the present disclosure with reference to appended drawings, the same or related constituting element is assigned the same reference number, and repeated descriptions thereof will be omitted.

One embodiment of the present disclosure relates to a method of preventing or managing dementia by estimating a dementia index using color data calculated based on time-series data from skin regions of interest of the left and right frontal lobes of a face image captured by an ordinary camera, an infrared camera, a thermal infrared camera, or a Time of Flight (TOF) camera; and analyzing dementia severity from the estimated dementia index. One embodiment of the present disclosure captures a face image and detects skin regions of interest (ROIs) of the left and right frontal lobes. As described above, one embodiment of the present disclosure relates to a method of measuring a dementia index using skin images of the left and right frontal lobes, analyzing dementia severity, and preventing or managing dementia. One embodiment of the present disclosure captures a face image and detects skin ROIs of the left and right frontal lobes from the captured face image.

One embodiment of the present disclosure uses detection models such as Haar cascade, Histogram of Oriented Gradients (HOG), Single Shot Multibox Detector (SSD), and You Only Look Once (YOLO) v3 to detect a face region from the images captured through an ordinary camera, an infrared camera, a thermal infrared camera, or a TOF camera. The embodiment changes setting values (e.g., a detection area limit, an input size, and a threshold) and selects a suitable detection model based on the environment in which an image is captured.

For example, each model shows a variation in detection performance according to the change in the lighting environment. In the case of face detection in a poor lighting environment, the YOLO model reveals the highest detection performance and extracts skin ROIs of the left and right frontal lobes from the detected face area. One embodiment of the present disclosure applies Fast Fourier Transform (FFT) to the Cg color signal calculated by converting the RGB color system of the detected skin ROIs of the left and right frontal lobes to the YCgCo color system and sets a dementia-related frequency band. One embodiment of the present disclosure calculates correlation coefficients by applying correlation analysis to real and imaginary values of frequency components calculated from the ROIs of the left frontal lobes and analyzes first dementia severity using the calculated correlation coefficients. And one embodiment of the present disclosure calculates the dementia index of the left frontal lobe using eigenvalues calculated by applying principal component analysis (PCA) to real and imaginary values of the same frequency components. In one embodiment of the present disclosure, an improved dementia index may be calculated by applying the calculated dementia index to the "left dementia index regression analysis formula DB," and secondary dementia severity is analyzed using the improved dementia index. One embodiment of the present disclosure may analyze dementia severity of the left frontal lobe using the first and second dementia severity analysis results. Also, one embodiment of the present disclosure calculates correlation coefficients by applying correlation analysis to the real and imaginary values of the frequency components calculated in the ROI of the right frontal lobe and analyzes third dementia severity using the calculated correlation coefficients. And one embodiment of the present disclosure calculates the dementia index of the right frontal lobe using eigenvalues calculated by applying principal component analysis (PCA) to real and imaginary values of the same frequency components. An improved dementia index may be calculated by applying the calculated dementia index to the "right dementia index regression analysis formula DB," and the fourth dementia severity is analyzed using the improved dementia index. One embodiment of the present disclosure may analyze the dementia severity of the right frontal lobe using the third and fourth dementia severity analysis results. One embodiment of the present disclosure may perform robust dementia severity analysis by applying a weighted average to the dementia severities of the left and right frontal lobes. Furthermore, one embodiment of the present disclosure may perform dementia index estimation and severity analysis in the skin regions of interest of the left and right frontal lobes from a captured face skin image based on various color systems. And one embodiment of the present disclosure may prevent/manage dementia by providing a biosignal-based customized sound source (for example, pulse and respiration) that matches the dementia index targeted by an individual based on a measured dementia index.

And one embodiment of the present disclosure applies a weighted average to the dementia severities of the left and right frontal lobes and uses the weighted average for estimating a dementia index based on non-contact skin images of frontal lobes which may be used for robust dementia severity analysis and for preventing or managing dementias by analyzing dementia severity from the estimated dementia index.

To achieve the technical object above, one embodiment of the present disclosure comprises capturing a face image using an ordinary camera, an infrared camera, a zoom camera, or the like; detecting skin regions of interest of the left and right frontal lobes from the captured face image; calculating average values of color data from the detected skin regions of interest of the left and right frontal lobes; applying Fast Fourier Transform (FFT) to the calculated average values of color data in the skin regions of interest of the left (or right) frontal lobe and setting a dementia-related frequency band; calculating correlation coefficients by applying correlation analysis to the real and imaginary parts of the frequency values calculated from the ROI of the left frontal lobe; analyzing first dementia severity using the calculated correlation coefficients; applying Principal Component Analysis (PCA) to the real and imaginary parts of the frequency values calculated from the ROI of the left frontal lobe and calculating a dementia index using the calculated eigenvalues; calculating an improved dementia index by applying the calculated dementia index to a "left dementia index regression analysis formula DB"; analyzing second dementia severity using the calculated dementia index; analyzing dementia severity of the left frontal lobe using the first and second dementia severity analysis results; calculating correlation coefficients by applying correlation analysis to the real and imaginary parts of the frequency values calculated from the ROI of the right frontal lobe; analyzing third dementia severity using the calculated correlation coefficients; applying Principal Component Analysis (PCA) to the real and imaginary parts of the frequency values calculated from the ROI of the right frontal lobe and calculating a dementia index using the calculated eigenvalues; calculating an improved dementia index by applying the calculated dementia index to a "right dementia index regression analysis formula DB"; analyzing fourth dementia severity using the calculated dementia index; analyzing dementia severity of the right frontal lobe using the third and fourth dementia severity analysis results; and analyzing robust dementia severity by applying a weighted average to the dementia severities of the left and right frontal lobes and preventing or managing dementia of an individual by utilizing the analysis result.

FIGS. 1A and 1B illustrate a process of measuring a dementia index using skin images of the left and right frontal lobes and analyzing dementia severity according to one embodiment of the present disclosure.

As shown in FIGS. 1A and 1B, an apparatus for dementia severity analysis according to one embodiment of the present disclosure captures a face image using a smart device equipped with a camera S101, detects a face region from the captured face image, sets regions of interest (ROIs) of the left and right frontal lobes S102, and sets skin regions of interest within the ROIs of the left and right frontal lobes S103. The apparatus for dementia severity analysis captures a region that adequately reflects an individual's condition, such as a face or skin, and detects skin region through a preprocessing step such as face detection and skin color detection. The apparatus for dementia severity analysis sets a region of interest from the detected skin region and extracts average color values of all (or part) of the pixels belonging to the corresponding region. In estimating a dementia index and analyzing dementia severity, various color systems may be used; in an example among various color systems according to one embodiment of the present disclosure, the RGB color system of a skin region is converted to the YCgCo color system, Fast Fourier Transform (FFT) is applied to the average values of Cg color data, and a dementia-related frequency band is set.

Also, it is possible to convert the RGB color system of the skin region to another color system. For example, the RGB color system may be converted into one of various color systems such as YUV, HSV, YCbCr, and YCgCo. In this case, color data may use one of the color difference components less affected by the surrounding environment (for example, illumination). For example, in the case of YCbCr, at least one of the Cb and Cr values may be used. In the case of YCgCo, at least one of the Cg and Co values may be used. Furthermore, one of the two color difference components, which is more robust to illumination changes, may be used. For example, in the case of YCgCo, only the Cg value may be used. In this case, a computer device may extract average values of the Cg color data of the skin region as color data. Furthermore, the color data may be obtained by applying weights to at least one or more color components in various color systems such as RGB, YUV, HSV, YCbCr, and YCgCo and combining the weighted color components. When color components are combined, color data may be obtained by adding different weights to color components according to a related color system and types of the color components. A face image based on the RGB color system may be changed to a related face image based on the YCgCo color system; in what follows, it may be assumed that the Cg value is obtained and used from the YCgCo system. The Cg value may be referred to as a Cg signal.

Dementia diagnosis methods based on existing EEG devices use EEG sensors attached to the frontal lobes of an individual; calculate Global Field Synchronization (GFS) and Global Synchronization Index (GSI) through analysis of frequency values (real and imaginary parts) in a dementia-related specific frequency band of a detected EEG signal; and provide a dementia diagnosis result from the calculation. At this time, the dementia-related specific frequency bands include theta, beta 1, beta 2, beta 3, and full space as a reliable frequency region through the P-value (a significance probability value in statistical hypothesis) shown in Table 1 below based on the index initially proposed in 2001 by Koening et al (Koening, T., Lehmann, D., Saito, N., Kuginuki, T., Kinoshita, T., Koukkou, M., 2001. Decreased functional connectivity of EEG theta-frequency activity in first-episode, neuroleptic-naive patients with schizophrenia: preliminary results. Schizophr. Res. 50, 55-60). The dementia severity may be judged by analyzing the frequency band.

TABLE 1

| Band | AD patient (N = 22) | Controls (N = 23) | P |
|---|---|---|---|
| Delta(1~3 Hz) | 0.547 ± 0.040 | 0.561 ± 0.036 | 0.190 |
| Theta(4~7 Hz) | 0.540 ± 0.023 | 0.555 ± 0.032 | 0.075 |
| Alpha(8~12 Hz) | 0.560 ± 0.055 | 0.575 ± 0.037 | 0.295 |
| Beta1(13~18 Hz) | 0.499 ± 0.026 | 0.523 ± 0.020 | 0.001 |
| Beta2(19~21 Hz) | 0.496 ± 0.027 | 0.514 ± 0.029 | 0.035 |
| Beta3(22~30 Hz) | 0.482 ± 0.021 | 0.505 ± 0.026 | 0.002 |
| Gamma(30~50 Hz) | 0.475 ± 0.041 | 0.486 ± 0.027 | 0.280 |
| Full(1~70 Hz) | 0.498 ± 0.019 | 0.514 ± 0.018 | 0.005 |

One embodiment of the present disclosure may use the proposed theta, beta, and the full frequency bands in estimating a dementia index using color data calculated in the skin regions of interest of the left and right frontal lobes and analyzing dementia severity; for example, the embodiment may estimate the dementia index using the frequency components of the theta (4-7 Hz) band and analyze dementia severity. The range of a dementia-related frequency band may be changed based on the image resolution, frame per second (fps), and so on.

The apparatus for analyzing dementia severity applies FFT to the average values of the color data calculated for the skin regions of interest of the left frontal lobe and sets a dementia-related frequency band S104. The apparatus for analyzing dementia severity calculates correlation coefficients by applying correlation analysis to the real and imaginary values of the frequency components calculated in the ROI of the left frontal lobe S105 and analyzes the first dementia severity using the calculated correlation coefficients S106. Also, the apparatus for analyzing dementia severity applies principal component analysis (PCA) to the real and imaginary values of the same frequency components S107 and calculates the dementia index of the left frontal lobe using the calculated eigenvalues S108. The apparatus for analyzing dementia severity may calculate an improved dementia index by applying the calculated dementia index to the "left dementia index regression analysis formula DB" S109 and analyze the second dementia severity using the calculated dementia index S110. The apparatus for analyzing dementia severity may analyze the dementia severity of the left frontal lobe using the first and second dementia severity analysis results S111.

On the other hand, the apparatus for analyzing dementia severity applies FFT to the average values of the color data calculated for the skin regions of interest of the right frontal lobe and sets a dementia-related frequency band S112. The apparatus for analyzing dementia severity calculates correlation coefficients by applying correlation analysis to the real and imaginary values of the frequency components calculated in the ROI of the right frontal lobe S113 and analyzes the third dementia severity using the calculated correlation coefficients S114. Also, the apparatus for analyzing dementia severity applies principal component analysis (PCA) to the real and imaginary values of the same frequency components S115 and calculates the dementia index of the right frontal lobe using the calculated eigenvalues S116. The apparatus for analyzing dementia severity may calculate an improved dementia index by applying the calculated dementia index to the "right dementia index regression analysis formula DB" S117 and analyze the fourth dementia severity using the calculated dementia index S118. The apparatus for analyzing dementia severity may analyze the dementia severity of the right frontal lobe using the third and fourth dementia severity analysis results S119. The apparatus for analyzing dementia severity may perform robust dementia severity analysis by applying a weighted average to the dementia severities of the left and right frontal lobes.

Figure 2:
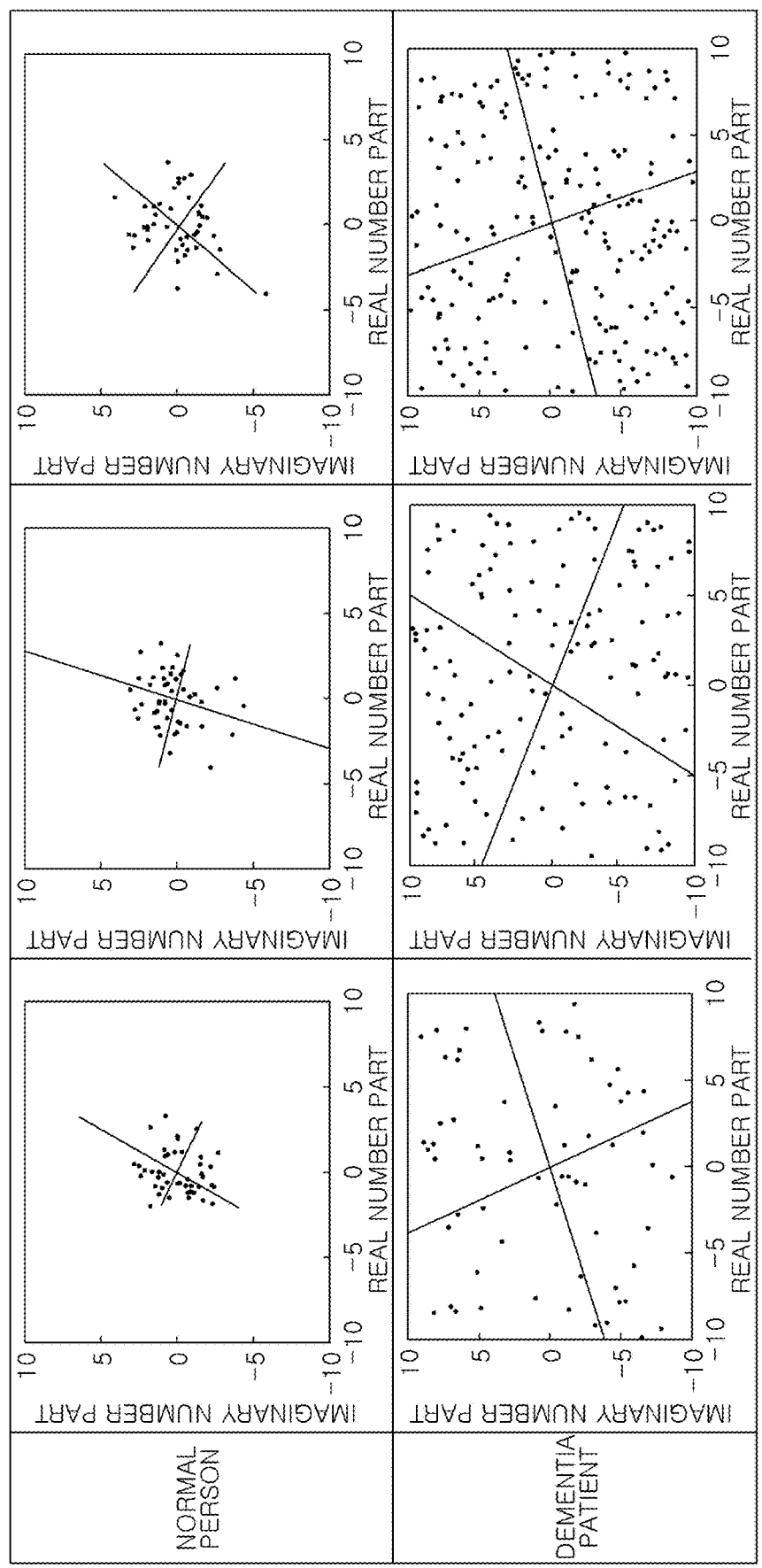
FIG. 2 illustrates an example in which PCA is applied to the frequency data of a dementia patient (x-axis: real number, y-axis: imaginary number).

FIG. 2 illustrates an example in which PCA is applied to the frequency data of a dementia patient (x-axis: real number, y-axis: imaginary number).

The dementia index represents dementia severity in a numerical value. FFT is applied to the average color data calculated in the skin regions of interest of the left and right frontal lobes to transform the average color data into the frequency domain. And for example, eigenvalues are calculated by applying principal component analysis (PCA) to the real and imaginary parts of the frequency components in the theta band (4-7 Hz). FIG. 2 illustrates the process described above.

The dementia index may be calculated by applying the two eigenvalues ($E_1$, $E_2$) calculated from the process of FIG. 2 to Eq. 1 below.

$$FDI(f) = \left| \frac{E(f)_1 - E(f)_2}{E(f)_3 + E(f)_3} \right| \quad \text{[Eq. 1]}$$

In Eq. 1, Facial Dementia Index (FDI) represents a dementia index calculated using the color data calculated in the left and right frontal lobes of a face image. The closer the dementia index is to 0, the higher the risk of dementia. On the other hand, as the dementia index becomes close to 1, it indicates a healthy state with a low risk of dementia. f represents a frequency band configured for the calculation of the dementia index. $E_1$ is an eigenvalue representing the components along the primary direction, and $E_2$ is an eigenvalue of the components orthogonal to $E_1$. Also, an improved dementia index may be calculated by applying the calculated dementia index to the "left and right dementia index regression analysis formula DB" (the left and right dementia index regression analysis formula DB will be described in detail with reference to FIG. 7).

Figure 3:
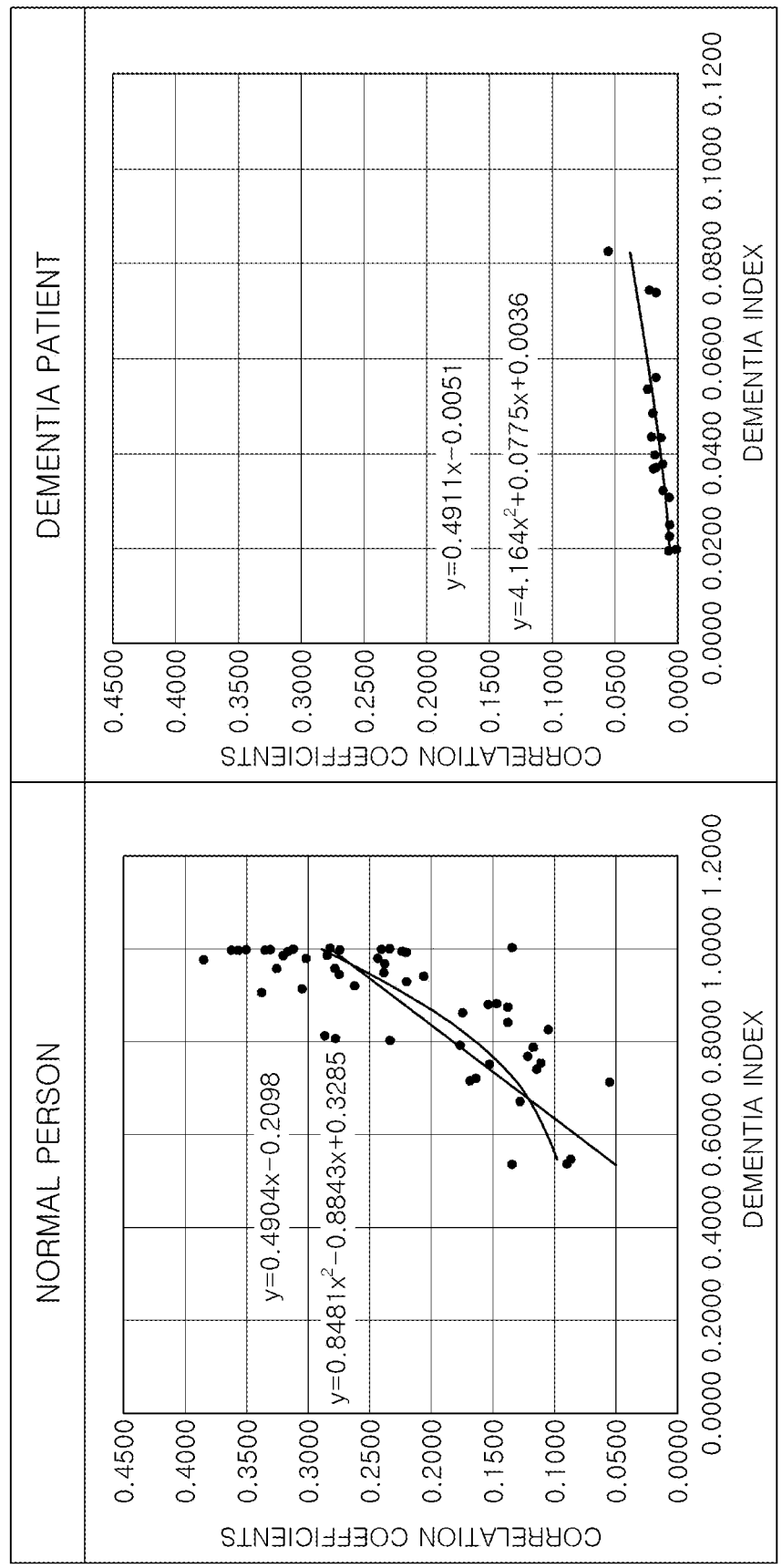
FIG. 3 illustrates dementia indexes (x-axis) and correlation coefficients (y-axis) calculated from a dementia patient and a normal person.

FIG. 3 illustrates dementia indexes (x-axis) and correlation coefficients (y-axis) calculated from a dementia patient and a normal person.

Refer to FIG. 3, dementia severity may be calculated using the calculated correlation coefficients and dementia index, where x-axis may represent the dementia index, and y-axis may represent the correlation coefficients.

Dementia severity may be analyzed using a correlation coefficient or a dementia index or both the correlation coefficient and the dementia index on the two-dimensional plane shown in FIG. 3. For example, dementia severity may be obtained using the ratio between the total number of distributed correlation coefficients calculated for the full region and the number of distributed correlation coefficients for each region. Table 2 shows the dementia severities obtained from the ratio described above.

TABLE 2

| Danger | Alert | Caution | Normal |
|---|---|---|---|
| $0 \leq x_{danger} < 0.05$ | $0.05 \leq x_{alert} < 0.1$ | $0.1 \leq x_{caution} < 0.15$ | $0.15 \leq x_{normal}$ |

Table 2 shows dementia severity analysis using correlation coefficients.

In Table 2, x represents the correlation coefficient distributed over the corresponding region (normal, caution, alert, danger), and thresholds of each region may vary depending on the data used.

As another example, dementia severity analysis using dementia indexes may provide dementia severity using the ratio between the total number of distributed dementia indexes calculated for the full region and the number of distributed dementia indexes calculated for each region. Table 3 shows the dementia severities obtained from the ratio described above.

TABLE 3

| Danger | Alert | Caution | Normal |
|---|---|---|---|
| $0 \leq x_{danger} < 0.2$ | $0.2 \leq x_{alert} < 0.4$ | $0.4 \leq x_{caution} < 0.6$ | $0.6 \leq x_{normal}$ |

Table 3 shows dementia severity analysis using a dementia index.

In Table 3, x represents the dementia index distributed over the corresponding region (normal, caution, alert, danger), and thresholds of each region may vary depending on the data used. Also, improved dementia severity analysis may be performed by applying a weighted average to the dementia severities calculated using the correlation coefficient and dementia index; and more robust dementia severity analysis may be performed by applying a weighted average to the dementia severities analyzed for the left and right frontal lobes. Furthermore, dementia index estimation and severity analysis may be performed using various color systems in the skin regions of interest of the left and right frontal lobes of captured facial skin images. And according to the analyzed dementia severity, dementia may be prevented/managed by providing a biosignal-based customized sound source (for example, pulse or respiration) that matches the dementia severity targeted by an individual.

Figure 4:
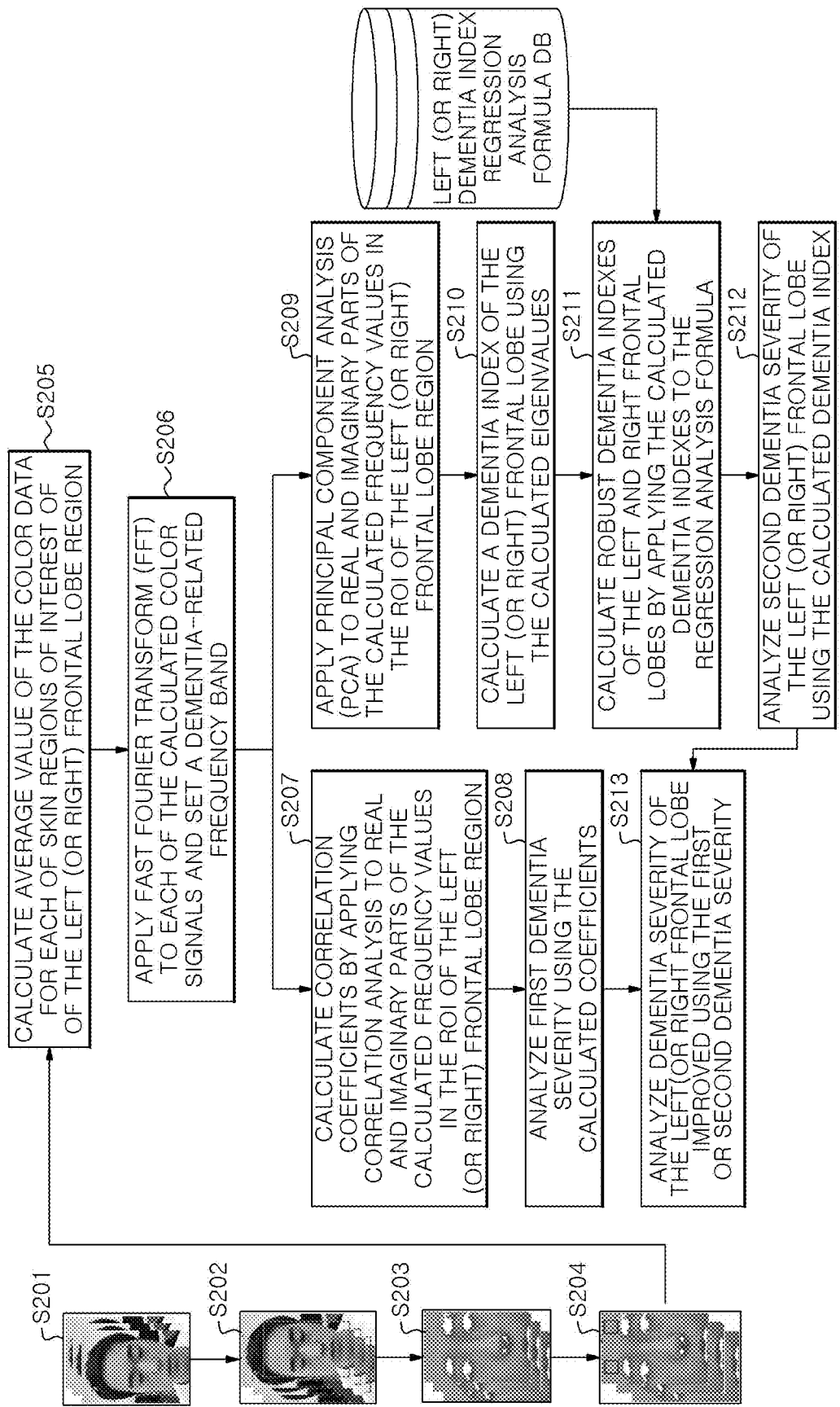
FIG. 4 illustrates a process of estimating a dementia index and dementia severity using skin images of the left (or right) frontal lobe according to one embodiment of the present disclosure.

FIG. 4 illustrates a process of estimating a dementia index and dementia severity using skin images of the left (or right) frontal lobe according to one embodiment of the present disclosure.

FIG. 4 is a conceptual representation of a dementia index estimation and dementia severity analysis process using a left (or right) frontal lobe skin image according to one embodiment of the present disclosure. The apparatus for analyzing dementia severity captures a face image using a smart device equipped with a camera S201. The apparatus for analyzing dementia severity captures an area that may adequately reflect an individual's condition, such as the face and skin, and then detects the skin through a pre-processing step such as face detection and skin color detection S202 and S203. The apparatus for analyzing dementia severity sets regions of interest from the detected skin region and detects the skin regions of interest of the left and right frontal lobe areas S204. The apparatus for analyzing dementia severity extracts the average color values of all (or part) of the pixels in the corresponding area S205. In estimating a dementia index and analyzing dementia severity, various color systems may be used; in an example among various color systems according to one embodiment of the present disclosure, the RGB color system of a skin region is converted to the YCgCo color system, Fast Fourier Transform (FFT) is applied to the average value of Cg color data, and a dementia-related frequency band is set S206.

And the apparatus for analyzing dementia severity calculates correlation coefficients by applying correlation analysis to the real and imaginary values of the frequency components calculated in the ROI of the left (or right) frontal lobe S207 and analyzes the first dementia severity using the calculated correlation coefficients S208. Also, the apparatus for analyzing dementia severity applies principal component analysis (PCA) to the real and imaginary values of the same frequency components S209 and calculates the dementia index of the left frontal lobe using the calculated eigenvalues S210. The apparatus for analyzing dementia severity may calculate an improved dementia index by applying the calculated dementia index to the "left (or right) dementia index regression analysis formula DB" S211 and analyze the second dementia severity using the calculated dementia index S212. The apparatus for analyzing dementia severity may analyze the dementia severity of the left (or right) frontal lobe using the first and second dementia severity analysis results S213.

Figure 5:
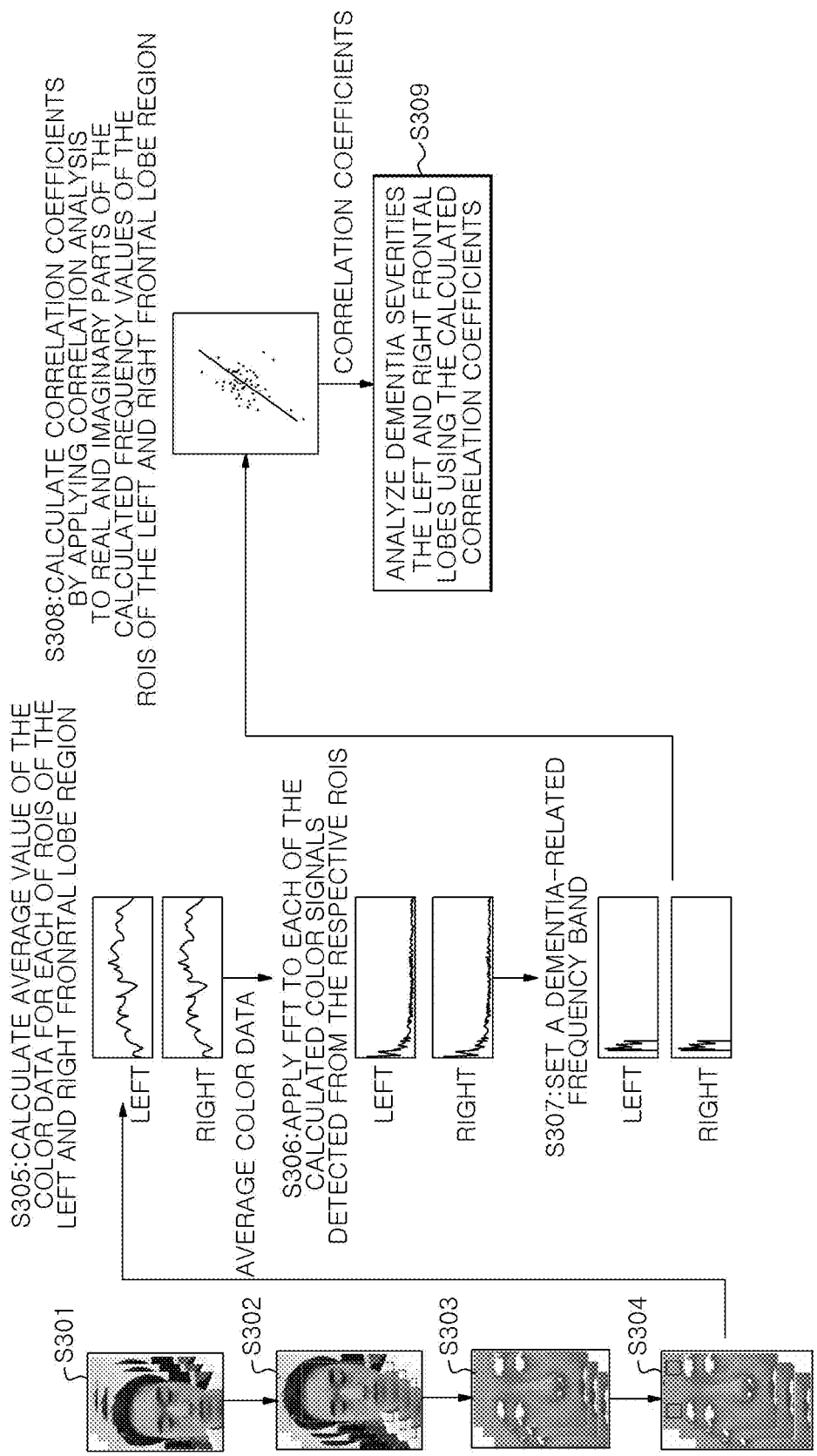
FIG. 5 illustrates a process of analyzing dementia severity using correlation coefficients calculated based on the color data of the left and right frontal lobes according to one embodiment of the present disclosure.

FIG. 5 illustrates a process of analyzing dementia severity using correlation coefficients calculated based on the color data of the left and right frontal lobes according to one embodiment of the present disclosure.

The apparatus for analyzing dementia severity according to one embodiment of the present disclosure captures a face image using a smart device equipped with a camera S301. The apparatus for analyzing dementia severity captures an area that may adequately reflect an individual's condition, such as the face and skin, and then detects the skin through a pre-processing step such as face detection and skin color detection S302 and S303. The apparatus for analyzing dementia severity sets regions of interest from the detected skin region and detects the skin regions of interest in the left and right frontal lobe areas S304. The apparatus for analyzing dementia severity calculates the average values of Cg color data respectively from the ROIs of the left and right frontal lobes by converting the RGB color system of the set regions of interest to the YCgCo color system S305. The apparatus for analyzing dementia severity applies Fast Fourier Transform (FFT) to the calculated average values of Cg color data and sets a dementia-related frequency band S306 and S307. And the apparatus for analyzing dementia severity calculates correlation coefficients by applying correlation analysis to the real and imaginary values of the frequency components calculated in the ROI of the left (or right) frontal lobe S308 and analyzes the left and right dementia severities by applying the calculated correlation coefficients to Table 2 above S309.

Figure 6:
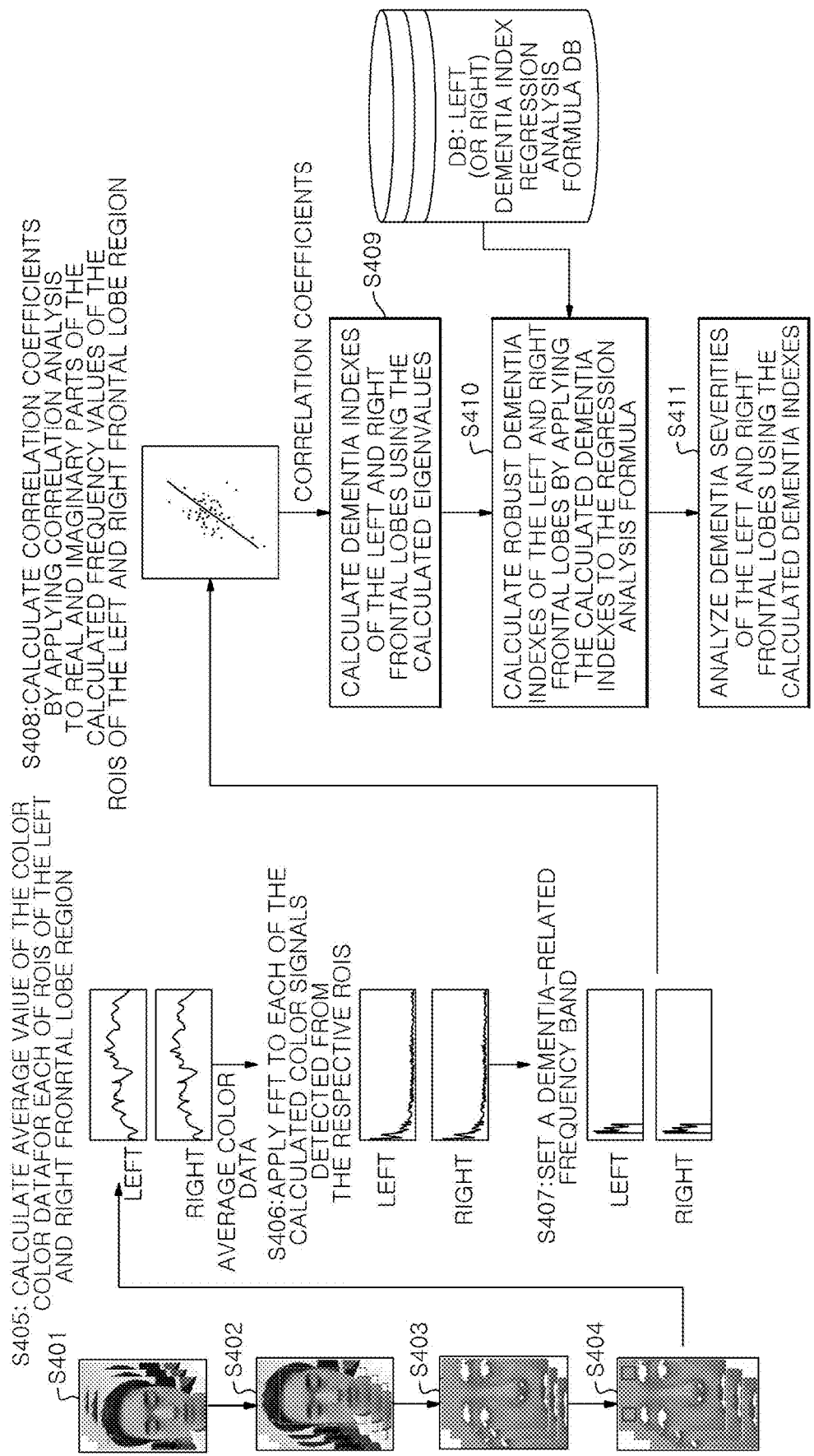
FIG. 6 illustrates a process of analyzing dementia severity using a dementia index calculated based on the color data of the left and right frontal lobes according to one embodiment of the present disclosure.

FIG. 6 illustrates a process of analyzing dementia severity using a dementia index calculated based on the color data of the left and right frontal lobes according to one embodiment of the present disclosure.

The apparatus for analyzing dementia severity according to one embodiment of the present disclosure captures a face image using a smart device equipped with a camera S401. The apparatus for analyzing dementia severity captures an area that may adequately reflect an individual's condition, such as the face and skin, and then detects the skin through a pre-processing step such as face detection and skin color detection S402 and S403. The apparatus for analyzing dementia severity sets regions of interest from the detected skin region and detects the skin regions of interest in the left and right frontal lobe areas S404. The apparatus for analyzing dementia severity calculates the average values of Cg color data respectively from the ROIs of the left and right frontal lobes by converting the RGB color system of the set regions of interest to the YCgCo color system S405. The apparatus for analyzing dementia severity applies Fast Fourier Transform (FFT) to the calculated average values of Cg color data and sets a dementia-related frequency band S406 and S407. And the apparatus for analyzing dementia severity calculates the dementia index of the left frontal lobe S409 using the eigenvalues calculated by applying principal component analysis (PCA) to the real and imaginary values of the frequency components calculated in the ROI of the left (or right) frontal lobe S408. The apparatus for analyzing dementia severity may calculate an improved dementia index by applying the calculated dementia index to the "left (or right) dementia regression analysis formula DB" S410 and analyzes dementia severities by applying the calculated improved dementia index to Table 3 above S411.

FIG. 7 illustrates a process of calculating an improved dementia index regression line (or curve) formula and storing the calculated formula in the "left (or right) dementia index regression analysis formula DB" according to one embodiment of the present disclosure.

The apparatus for analyzing dementia severity according to one embodiment of the present disclosure captures a face image using a smart device equipped with a camera S501 and at the same time, measures EEG signals of the left and right frontal lobes using an EEG measurement device. The apparatus for analyzing dementia severity captures an area that may adequately reflect an individual's condition, such as the face and skin, and then detects the skin through a pre-processing step such as face detection and skin color detection S502 and S503. The apparatus for analyzing dementia severity sets regions of interest from the detected skin region and detects the skin regions of interest in the left and right frontal lobe areas S504. The apparatus for analyzing dementia severity calculates the average values of Cg color data respectively from the ROIs of the left and right frontal lobes by converting the RGB color system of the set regions of interest to the YCgCo color system S505. The apparatus for analyzing dementia severity applies Fast Fourier Transform (FFT) to the calculated average values of Cg color data and sets a dementia-related frequency band S506. The apparatus for analyzing dementia severity calculates the dementia index of the left frontal lobe S508 using the eigenvalues calculated by applying principal component analysis (PCA) to the real and imaginary values of the frequency components in the set frequency band S508. The apparatus for analyzing dementia severity stores the calculated dementia index in a "DB of dementia index estimated from the left (or right) frontal lobe images" S509 and stores a dementia index calculated through frequency analysis of EEG signals calculated from the EEG device in a "DB of dementia index measured by the EEG device" S510. And the apparatus for analyzing dementia severity calculates a regression line (or regression curve) formula by applying regression analysis to the dementia index of the left (or right) frontal lobe calculated from the face image and the EEG device and stores the calculated regression line (or regression curve) formula in a "left (or right) dementia index regression analysis formula DB" S511.

A linear function obtained by representing a set of points on a scatter diagram by a straight line models the relationship between two variables, and one embodiment of the present disclosure derives a regression line equation using the "DB of dementia index estimated from the left (or right) frontal lobe of a face image" and the "DB of dementia index measured using the EEG device." The equation of the regression line is shown in Eq. 2.

$$y=ax+b \quad [\text{Eq.2}]$$

In Eq. 2, y represents an improved dementia index, and x represents the dementia index estimated from the left (or right) frontal lobe of a face image. For the results obtained by applying actual data, the constants a and b may be changed depending on the data used.

A quadratic function obtained by representing a set of points on a scatter diagram by a curved line models the relationship between two variables, and one embodiment of the present disclosure derives a regression line equation using the "DB of dementia index estimated from the left (or right) frontal lobe of a face image" and the "DB of dementia index measured using the EEG device." The equation of the regression curve is shown in Eq. 3.

$$y=ax^2+bx+c \quad [\text{Eq.3}]$$

In Eq. 3, y represents an improved dementia index, and x represents the dementia index estimated from the left (or right) frontal lobe of a face image. For the results obtained by applying actual data, the constants a, b, and c may be changed depending on the data used. Also, other types of regression functions may be applied in addition to the regression line (or regression curve).

Figure 8A:
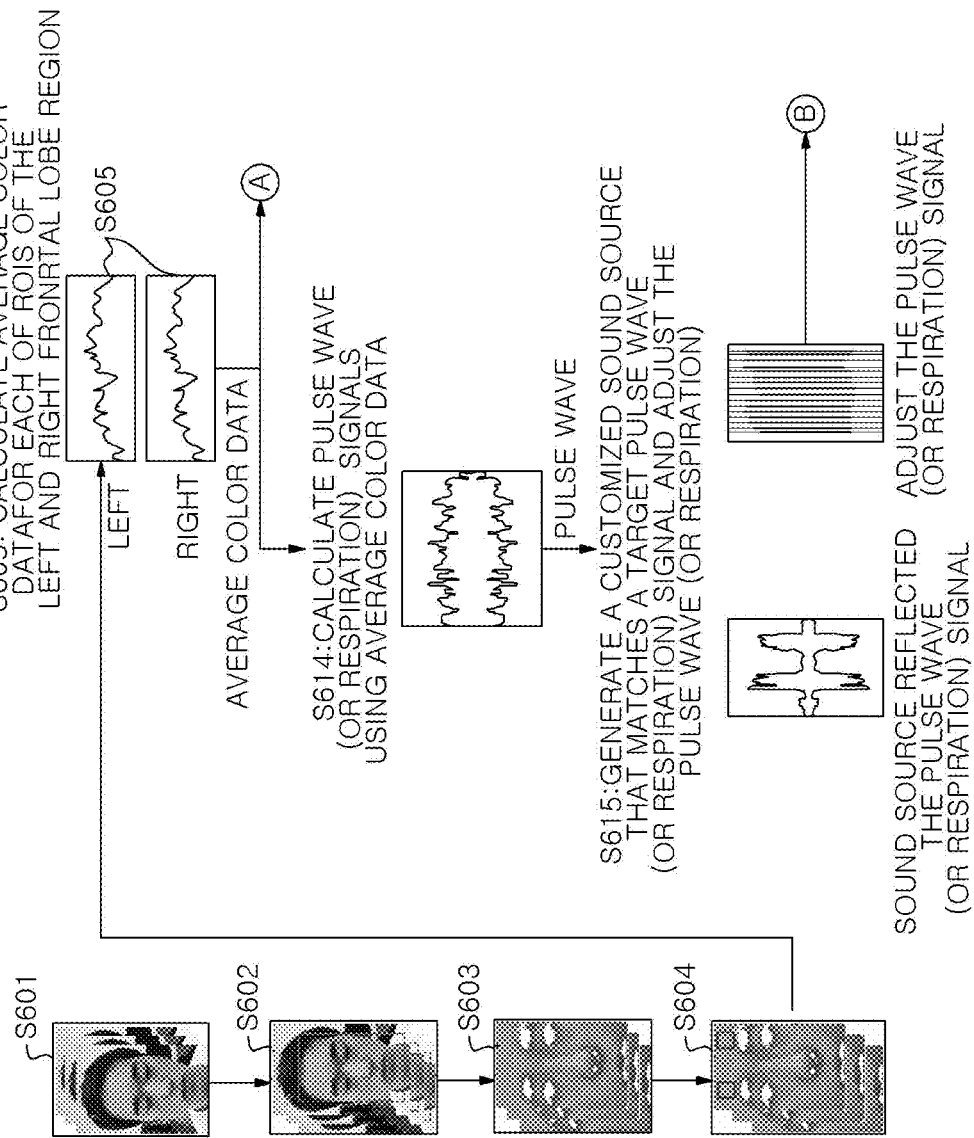
FIGS. 8A and 8B illustrate a process of preventing or managing dementia based on the dementia severity indicated using correlation coefficients and dementia index according to one embodiment of the present disclosure.
Figure 8B:
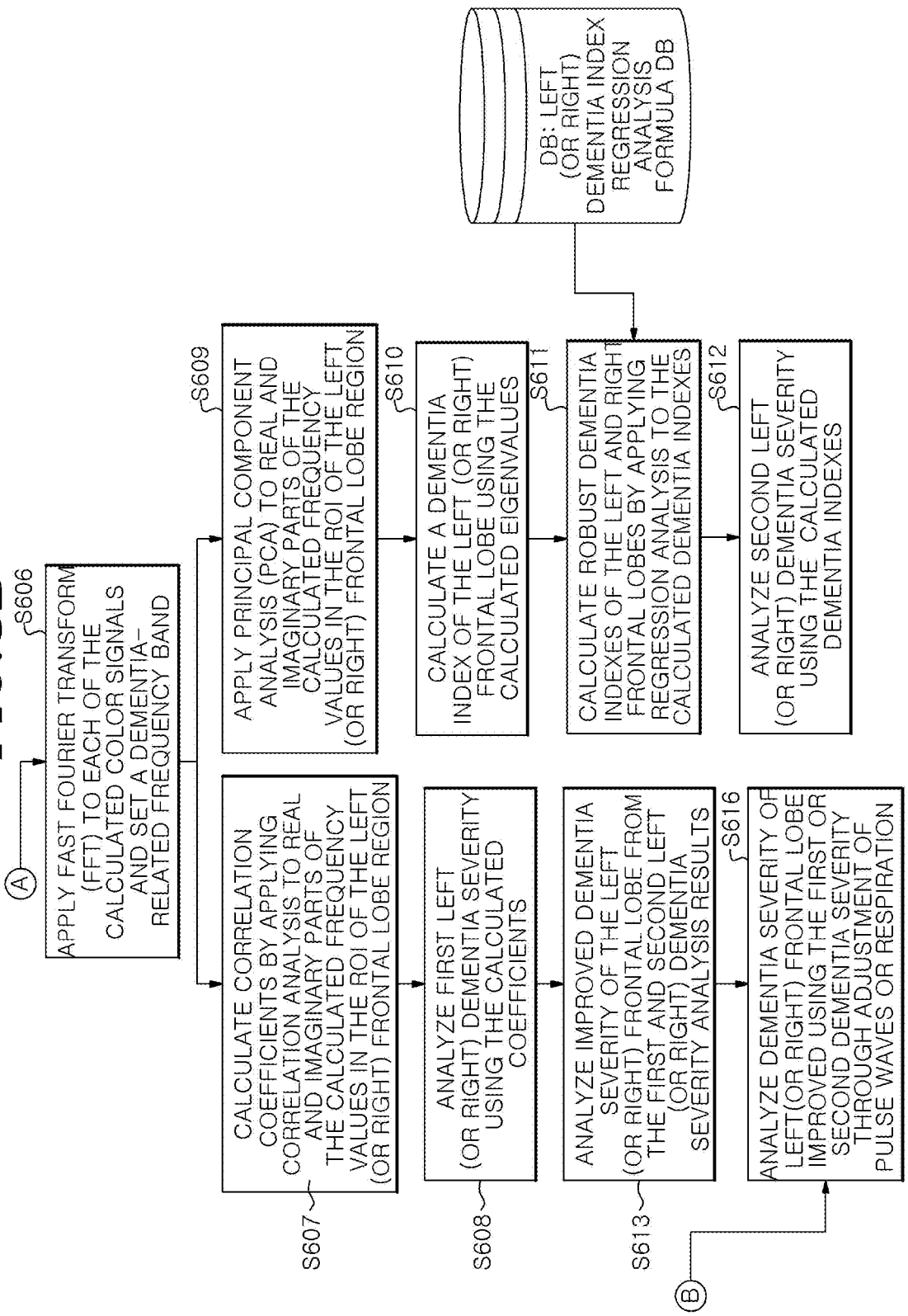

FIGS. 8A and 8B illustrates a process of preventing or managing dementia based on the dementia severity indicated using correlation coefficients and dementia index according to one embodiment of the present disclosure.

For example, one embodiment of the present disclosure may prevent/manage the dementia index through music reflecting biosignals.

The apparatus for analyzing dementia severity captures a face image using a smart device equipped with a camera S601. The apparatus for analyzing dementia severity captures an area that may adequately reflect an individual's condition, such as the face and skin, and then detects the skin through a pre-processing step such as face detection and skin color detection S602 and S603. The apparatus for analyzing dementia severity sets regions of interest from the detected skin region and detects the skin regions of interest in the left and right frontal lobe areas S604. The apparatus for analyzing dementia severity extracts average color values of all (or part) of the pixels belonging to the corresponding region S605. In estimating a dementia index and analyzing dementia severity, various color systems may be used; in an example among various color systems according to one embodiment of the present disclosure, the RGB color system of a skin region is converted to the YCgCo color system, Fast Fourier Transform (FFT) is applied to the average value of Cg color data, and a dementia-related frequency band is set S606.

And the apparatus for analyzing dementia severity calculates correlation coefficients by applying correlation analysis to the real and imaginary values of the frequency components calculated in the ROI of the left (or right) frontal lobe S607 and analyzes the first dementia severity using the calculated correlation coefficients S608. Also, the apparatus for analyzing dementia severity applies principal component analysis (PCA) to the real and imaginary values of the same frequency components S609 and calculates the dementia index of the left frontal lobe using the calculated eigenvalues S610. The apparatus for analyzing dementia severity calculates an improved dementia index by applying the calculated dementia index to the "left (or right) dementia index regression analysis formula DB" S611 and analyzes the second dementia severity using the calculated dementia index S612. The apparatus for analyzing dementia severity may analyze the dementia severity of the left frontal lobe using the first and second dementia severity analysis results S613.

At the same time, the apparatus for analyzing dementia severity calculates a pulse wave (or respiration) signal calculated using the skin color data S614 and tunes biosignals by providing a customized sound source reflecting an individual's biosignals (for example, a pulse wave signal or a respiration signal) that matches the dementia severity targeted by the individual S615, thereby preventing or managing dementia. Also, the apparatus for analyzing dementia severity may manage dementia through biosignal-based adjustment of pulse waves or respiration that matches the dementia severity targeted by the individual according to the analyzed dementia severity.

Meanwhile, an experiment for dementia index estimation and dementia severity analysis using skin images of the frontal lobes according to one embodiment of the present disclosure will be described.

An experiment for comparing dementia indexes and severities calculated from face images of a normal person and skin images of the frontal lobes of a dementia patient were conducted to check the performance of the method for estimating dementia index and analyzing dementia severity using skin images of the frontal lobes.

One embodiment of the present disclosure captures a face image using an ordinary camera, an infrared camera, a thermal infrared camera, or a TOF camera; and detects skin regions of interest of the left and right frontal lobes. Fast Fourier Transform (FFT) is applied to the Cg color signal calculated by converting the RGB color system of the detected skin regions of interest of the left and right frontal lobes into the YCgCo color system and sets a dementia-related frequency band. Correlation coefficients are calculated by applying correlation analysis to the real and imaginary values of the frequency components calculated in the ROIs of the left frontal lobe, and the first dementia severity using the calculated correlation coefficients is analyzed. And the dementia index of the left frontal lobe is calculated using the eigenvalues calculated by applying principal component analysis (PCA) to the real and imaginary values of the same frequency components. An improved dementia index may be calculated by applying the calculated dementia index to the "left dementia index regression analysis formula DB," and the second dementia severity is analyzed using the improved dementia index calculated. And the dementia severity of the left frontal lobe may be analyzed using the first and second dementia severity analysis results. Also, correlation coefficients are calculated by applying correlation analysis to the real and imaginary values of the frequency components calculated in the ROI of the right frontal lobe, and the third dementia severity is analyzed using the calculated correlation coefficient. And the dementia index of the right frontal lobe is calculated using eigenvalues calculated by applying principal component analysis (PCA) to real and imaginary values of the same frequency components. An improved dementia index may be calculated by applying the calculated dementia index to the "right dementia index regression analysis formula DB," and the fourth dementia severity is analyzed using the improved dementia index. And the dementia severity of the right frontal lobe is analyzed using the third and fourth dementia severity analysis results. And robust dementia severity is calculated and compared by applying a weighted average to the dementia severities of the left and right frontal lobes.

In the experiment, the dementia index and correlation coefficients were calculated using face images of a normal person and a dementia patient captured for 1 minute per session, from which the dementia severity was analyzed. Image capture was conducted at 30 frames per second. The dementia index and dementia severity calculated from a total of 40 face skin images of the normal person and the dementia patient were compared.

Figure 9:
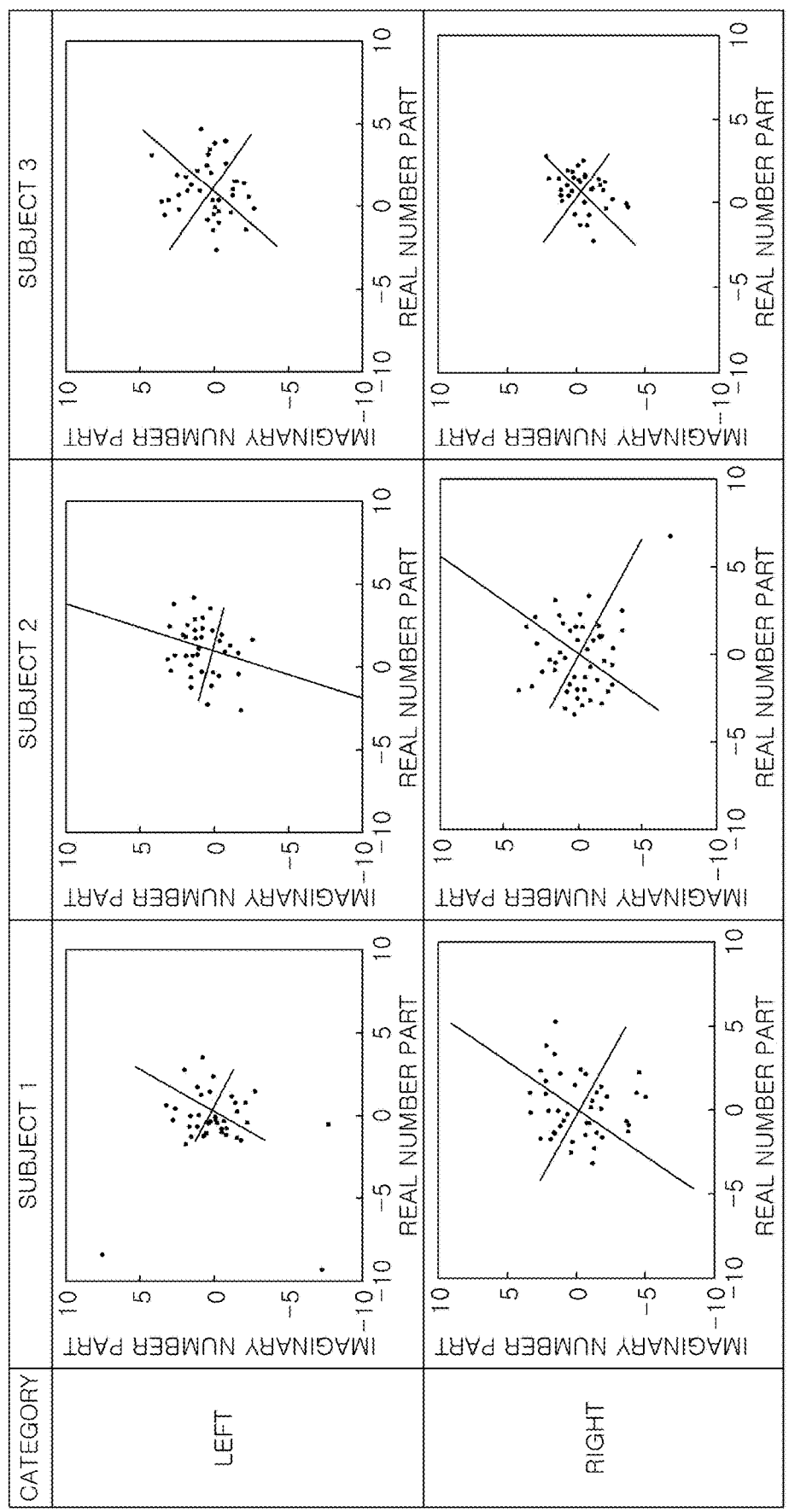
FIG. 9 illustrates a real number part (x-axis) and an imaginary number part (y-axis) of the frequency values calculated from a face image of a normal person.

FIG. 9 illustrates a real number part (x-axis) and an imaginary number part (y-axis) of the frequency values calculated from a face image of a normal person.

FIG. 9 shows a two-dimensional plane depicting the real and imaginary number parts calculated from the frequency values of the left and right frontal lobes of face images of a normal person captured for 1 minute.

Figure 10:
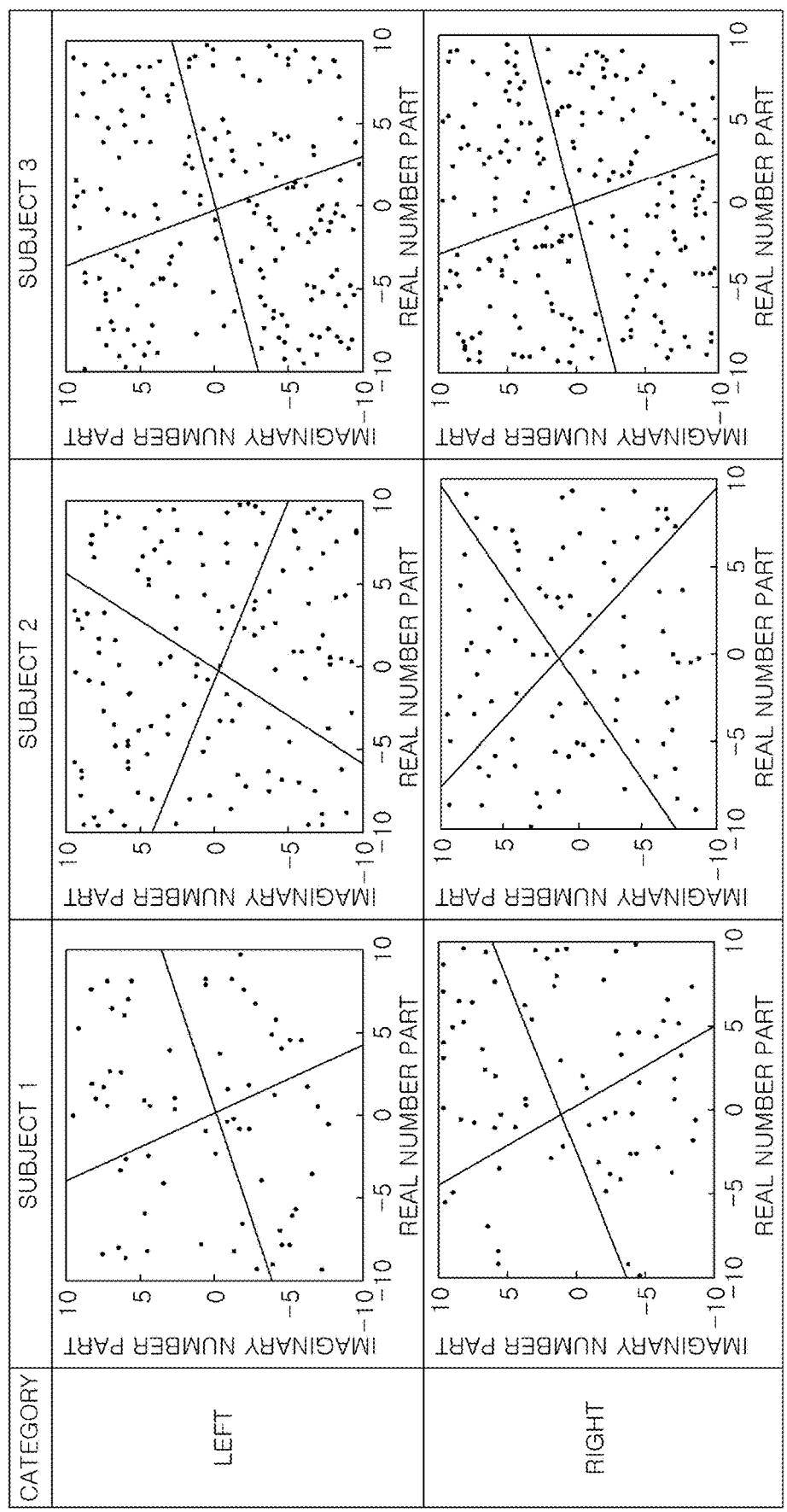
FIG. 10 illustrates a real number part (x-axis) and an imaginary number part (y-axis) of the frequency values calculated from a face image of a dementia patient.

FIG. 10 illustrates a real number part (x-axis) and an imaginary number part (y-axis) of the frequency values calculated from a face image of a dementia patient.

FIG. 10 shows a two-dimensional plane depicting the real and imaginary number parts calculated from the frequency values of the left and right frontal lobes of face images of a dementia patient captured for 1 minute.

The two-dimensional planes of FIGS. 9 and 10 provide comparative displays of real and imaginary parts of frequency values within a dementia-related frequency band based on the color data calculated from the skin regions of interest of the left and right frontal lobes calculated from a normal person and a dementia patient.

In estimating the dementia index using the skin images of the left and right frontal lobes, one embodiment of the present disclosure may capture face images using a smart device owned by an individual without involving a separate hardware module, extract color signals through face detection and skin regions of interest of the left and right frontal lobes, and estimate the dementia index and analyze the dementia severity using the extracted signals.

The method above may provide a fast and convenient dementia index estimation system for general individuals. Also, it is possible to estimate the dementia index and analyze the dementia severity in a shorter measurement time than the conventional method.

Figure 11:
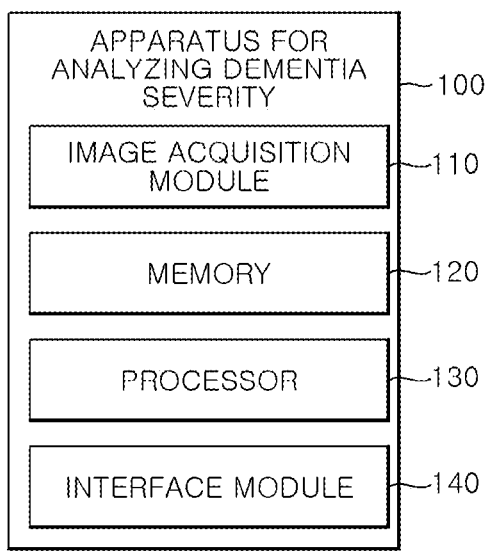
FIG. 11 illustrates a structure of an apparatus for analyzing dementia severity using skin images of the frontal lobes according to one embodiment of the present disclosure.

FIG. 11 illustrates a structure of an apparatus for analyzing dementia severity using skin images of the frontal lobes according to one embodiment of the present disclosure.

As shown in FIG. 11, the apparatus for analyzing dementia severity 100 using skin images of the frontal lobes according to one embodiment of the present disclosure includes an image acquisition module 110, a memory 120, and a processor 130. The apparatus for analyzing dementia severity 100 may further include an interface module 140. However, not all of the illustrated components are essential components. The apparatus for analyzing dementia severity 100 may be implemented using more components than the illustrated components, and at the same time, the apparatus for analyzing dementia severity 100 may still be implemented using fewer components.

In what follows, specific structure and operations of individual constituting elements of the apparatus for analyzing dementia severity 100 of FIG. 11 will be described.

The image acquisition module 110 captures face images through an ordinary camera, an infrared camera, a thermal infrared camera, or a Time of Flight (TOF) camera.

The memory 120 stores one or more programs related to a dementia severity analysis operation using the frontal lobe skin images.

The processor 130 executes one or more programs stored in the memory 120. The processor 130 calculates color data from skin regions of interest of the frontal lobe area in the captured face image, calculates frequency values corresponding to a dementia-related frequency band using the calculated color data, and analyzes the dementia severity using the calculated frequency values.

Based on the embodiments, the processor 130 may analyze the first dementia severity using the frequency values calculated by applying FFT to the average color data calculated for the skin regions of interest detected from the left frontal lobe area, analyze the second dementia severity using the calculated frequency values, and analyze the improved dementia severity of the left frontal lobe from the first and second dementia severity analysis results.

Based on the embodiments, the processor 130 may calculate correlation coefficients by applying correlation analysis to the real and imaginary parts of the frequency values calculated by applying FFT to the average color data calculated for the skin regions of interest of the left frontal lobe and analyze the first dementia severity using the calculated correlation coefficients.

Based on the embodiments, the processor 130 may calculate the dementia index of the left frontal lobe by applying principal component analysis to the frequency values calculated by applying FFT to the average color data calculated for the skin regions of interest of the left frontal lobe and analyze the second dementia severity using the calculated dementia index of the left frontal lobe.

Based on the embodiments, the processor 130 may calculate the eigenvalues by applying principal component analysis to the real and imaginary parts of the frequency values calculated by applying FFT to the average color data calculated for the skin regions of interest of the left frontal lobe and calculate the dementia index of the left frontal lobe using the calculated eigenvalues.

Based on the embodiments, the processor 130 may calculate the robust dementia index of the left frontal lobe by applying the calculated dementia index of the left frontal lobe to the regression analysis formula and analyze the second dementia severity using the robust dementia index of the left frontal lobe.

Based on the embodiments, the processor 130 may analyze the third dementia severity using the frequency values calculated by applying FFT to the average color data calculated for the skin regions of interest of the right frontal lobe area, analyze the fourth dementia severity using the calculated frequency values, and analyze the improved dementia severity of the right frontal lobe from the third and fourth dementia severity analysis results.

Based on the embodiments, the processor 130 may calculate correlation coefficients by applying correlation analysis to the real and imaginary parts of the frequency values calculated by applying FFT to the average color data calculated for the skin regions of interest of the right frontal lobe and analyze the third dementia severity using the calculated correlation coefficients.

Based on the embodiments, the processor 130 may calculate the dementia index of the right frontal lobe by applying principal component analysis to the frequency values calculated by applying FFT to the average color data calculated for the skin regions of interest of the right frontal lobe and analyze the fourth dementia severity using the calculated dementia index of the right frontal lobe.

Based on the embodiments, the processor 130 may calculate the eigenvalues by applying principal component analysis to the real and imaginary parts of the frequency values calculated by applying FFT to the average color data calculated for the skin regions of interest of the right frontal lobe and calculate the dementia index of the right frontal lobe using the calculated eigenvalues.

Based on the embodiments, the processor 130 may calculate the robust dementia index of the right frontal lobe by applying the calculated dementia index of the right frontal lobe to the regression analysis formula and analyze the fourth dementia severity using the robust dementia index of the right frontal lobe.

Meanwhile, based on the embodiments, the interface module 140 provides a dementia management interface to a user. The processor 130 may calculate biosignals using calculated color data and manage dementia by providing, through the interface module 140, a biosignal-based customized sound source that matches the dementia severity targeted by an individual based on the analyzed dementia severity.

Based on the embodiments, the processor 130 may calculate biosignals using calculated color data and manage dementia by providing, through the interface module 140, a biosignal-based pulse wave or respiration adjustment training that matches the dementia severity targeted by an individual based on the analyzed dementia severity.

Meanwhile, a non-transitory computer-readable storage medium for storing instructions instructing the processor to execute the method may be provided, the method comprising calculating color data from skin regions of interest of the frontal lobe area; calculating frequency values corresponding to a dementia-related frequency band using the calculated color data; and analyzing dementia severity using the calculated frequency values.

Meanwhile, based on one embodiment of the present disclosure, various embodiments described above may be implemented by software that includes instructions stored in a machine (for example, a computer)-readable storage medium. The machine is an apparatus capable of calling stored commands from the storage medium and operating according to the commands called, which may include an electronic device (for example, an electronic device (A)) according to the disclosed embodiments. When a command is executed by the processor, the processor may perform the function corresponding to the command directly or by using other constituting elements under the control of the processor. The command may include code generated or executed by a compiler or an interpreter. The machine-readable storage medium may be provided in the form of a non-transitory storage medium. Here, the term "non-transitory" only indicates that the storage medium does not include a signal and is tangible but does not distinguish whether data are stored semi-permanently or temporarily.

Also, according to one embodiment of the present disclosure, the method according to various embodiments described above may be provided by being included in a computer program product. The computer program product may be traded between sellers and buyers as a commodity. The computer program product may be distributed in the form of a machine-readable storage medium (for example, a Compact Disc Read Only Memory (CD-ROM)) or online through an application store (for example, Play Store™). In the case of online distribution, at least part of the computer program product may be at least stored temporarily or generated temporarily in a server of the manufacturer, a server of the application store, or a storage medium such as a memory of a relay server.

Also, according to one embodiment of the present disclosure, various embodiments described above may be implemented in a recording medium that may be read by a computer or a machine similar thereto by using software, hardware, or a combination of both. In some cases, the embodiments of the present disclosure may be implemented within a processor itself. In the case of software implementation, the embodiments such as procedures and functions according to the present disclosure may be implemented by separate software modules. Each of the software modules may perform one or more functions and operations according to the present disclosure.

The computer instructions for executing processing operations of the machine according to various embodiments described above may be stored in a non-transitory computer-readable medium. When executed by a processor of a specific machine, the computer instructions stored in the non-transitory computer-readable medium command the specific machine to perform processing operations for an apparatus according to the various embodiments described above. The non-transitory computer-readable medium refers to a medium that stores data semi-permanently and that may be read by a machine, rather than a medium that stores data for a short time period such as a register, a cache, and a memory. Specific examples of the non-transitory computer-readable medium include a CD, a DVD, a hard disk, a Bluray disk, a USB memory, a memory card, and a ROM.

Also, each of the constituting elements (for example, a module or a program) according to the various embodiments of the present disclosure may be composed of a single or multiple entities; and part of the corresponding sub-elements described above may be omitted, or another sub-element may be further included in the various embodiments. Alternatively or additionally, part of the constituting elements (for example, a module or a program) may be integrated into a single entity, and the functions executed by the respective constituting elements prior to the integration may be performed in the same manner or in a similar manner. The operations executed by a module, a program, or another constituting element according to the various embodiments may be performed in a sequential, parallel, or heuristic manner; or at least part of the operations may be performed in a different order or omitted, or another operation may be added to the operations.

Throughout the document, preferred embodiments of the present disclosure have been described with reference to appended drawings; however, the present disclosure is not limited to the embodiments above. Rather, it should be noted that various modifications of the present disclosure may be made by those skilled in the art to which the present disclosure belongs without leaving the technical scope of the present disclosure defined by the appended claims, and these modifications should not be understood individually from the technical principles or perspectives of the present disclosure.

What is claimed is:

1. A method for analyzing dementia severity, the method comprising:
    calculating color data from skin regions of interest of a frontal lobe region;
    calculating frequency values corresponding to a frequency band of a dementia-related biosignal based on the calculated color data;
    analyzing dementia severity using the calculated frequency values, and
    preventing or managing dementia of an individual using the analyzed dementia severity.

2. The method of claim 1, wherein the analyzing dementia severity includes analyzing a first dementia severity for detected skin regions of interest of a left frontal lobe region of the frontal lobe region using the frequency values calculated by applying Fast Fourier Transform (FFT) to an average value of the color data calculated within the skin regions of interest, analyzing a second dementia severity using the calculated frequency values, and analyzing an improved dementia severity of the left frontal lobe based on results of analyzing the first and the second dementia severity.

3. The method of claim 2, wherein the analyzing dementia severity includes calculating correlation coefficients by applying correlation analysis to real and imaginary parts of the frequency values calculated by applying FFT to the average value of the color data calculated within the skin regions of interest of the left frontal lobe region and analyzing the first dementia severity using the calculated correlation coefficients.

4. The method of claim 2, wherein the analyzing dementia severity includes calculating a dementia index of the left frontal lobe by applying principal component analysis to the frequency values calculated by applying FFT to the average value of the color data calculated within the skin regions of interest of the left frontal lobe region and analyzing the second dementia severity using the calculated dementia index of the left frontal lobe.

5. The method of claim 4, wherein the analyzing dementia severity includes calculating eigenvalues by applying principal component analysis to real and imaginary parts of the frequency values calculated by applying FFT to the average value of the color data calculated within the skin regions of interest of the left frontal lobe region and calculating the dementia index of the left frontal lobe using the calculated eigenvalues.

6. The method of claim 4, wherein the analyzing dementia severity includes calculating a robust dementia index of the left frontal lobe by applying the calculated dementia index of the left frontal lobe to a regression analysis formula and analyzing the second dementia severity using the robust dementia index of the left frontal lobe.

7. The method of claim 1, wherein the analyzing dementia severity includes analyzing a third dementia severity using the frequency values calculated by applying FFT to an average value of the color data calculated within the skin regions of interest of a right frontal lobe region of the frontal lobe region, analyzing a fourth dementia severity using the calculated frequency values, and analyzing an improved dementia severity of a right frontal lobe based on results of analyzing the third and the fourth dementia severity.

8. The method of claim 7, wherein the analyzing dementia severity includes calculating correlation coefficients by applying correlation analysis to real and imaginary parts of the frequency values calculated by applying FFT to the average value of the color data calculated within the skin regions of interest of the right frontal lobe region and analyzing the third dementia severity using the calculated correlation coefficients.

9. The method of claim 7, wherein the analyzing dementia severity includes calculating a dementia index of the right frontal lobe by applying principal component analysis to the frequency values calculated by applying FFT to the average value of the color data calculated within the skin regions of interest of the right frontal lobe region and analyzing the fourth dementia severity using the calculated dementia index of the right frontal lobe.

10. The method of claim 9, wherein the analyzing dementia severity includes calculating eigenvalues by applying principal component analysis to real and imaginary parts of the frequency values calculated by applying FFT to the average value of the color data calculated within the skin regions of interest of the right frontal lobe region and calculating a dementia index of the right frontal lobe using the calculated eigenvalues.

11. The method of claim 9, wherein the analyzing dementia severity includes calculating a robust dementia index of the right frontal lobe by applying the calculated dementia index of the right frontal lobe to a regression analysis formula and analyzing the fourth dementia severity using the robust dementia index of the right frontal lobe.

12. The method of claim 1, further comprising calculating biosignal based on the calculated color data and providing a biosignal-based customized sound source corresponding to a dementia severity targeted by the user based on the analyzed dementia severity.

13. The method of claim 1, further comprising calculating biosignal using the calculated color data and providing information on a biosignal-based pulse wave or respiration adjustment training corresponding to a dementia severity targeted by the user based on the analyzed dementia severity.

14. An apparatus for analyzing dementia severity, the apparatus comprising:
an image acquisition module capturing a face image;
a memory storing one or more programs related to a dementia severity analysis operation using frontal lobe skin images; and
a processor executing the stored one or more programs, wherein the processor is configured to:
calculate color data from skin regions of interest of a frontal lobe region extracted within the face image;
calculate frequency values corresponding to a frequency band of a dementia-related biosignal based on the calculated color data;
analyze dementia severity using the calculated frequency values; and
prevent or manage dementia of an individual using the analyzed dementia severity.

15. The apparatus of claim 14, wherein the processor is configured to analyze a first dementia severity for extracted skin regions of interest of a left frontal lobe region of the frontal lobe region using the frequency values calculated by applying Fast Fourier Transform (FFT) to an average value of the color data calculated within the skin regions of interest, analyze a second dementia severity using the calculated frequency values, and analyze an improved dementia severity of the left frontal lobe based on results of analyzing the first and the second dementia severity.

16. The apparatus of claim 15, wherein the processor is configured to calculate correlation coefficients by applying correlation analysis to real and imaginary parts of the frequency values calculated by applying FFT to the average value of the color data calculated within the skin regions of interest of the left frontal lobe region and analyze the first dementia severity using the calculated correlation coefficients.

17. The apparatus of claim 15, wherein the processor is configured to analyze a third dementia severity for extracted skin regions of interest of a right frontal lobe region of the frontal lobe region using the frequency values calculated by applying Fast Fourier Transform (FFT) to an average value of the color data calculated within the skin regions of interest of the right frontal lobe region, analyze a fourth dementia severity using the checked frequency values, and analyze an improved dementia severity of the right frontal lobe based on results of analyzing the third and the fourth dementia severity.

18. The apparatus of claim 14,
wherein the processor is configured to calculate a biosignal based on the calculated color data and provide a biosignal-based customized sound source to a user corresponding to a dementia severity targeted by the user based on the analyzed dementia severity for the user.

19. The apparatus of claim 14,
wherein the processor is configured to calculate a biosignal based on the calculated color data and provide information on a biosignal-based pulse wave or respiration adjustment training to a user corresponding to dementia severity targeted by the user based on the analyzed dementia severity for the user.

20. A non-transitory computer-readable storage medium storing instructions instructing the processor to execute a method, the method comprising:
calculating color data from skin regions of interest of a frontal lobe region extracted within the face image;
calculating frequency values corresponding to a frequency band of a dementia-related biosignal based on the calculated color data;
analyzing dementia severity using the calculated frequency values; and
preventing or managing dementia of an individual using the analyzed dementia severity.

\* \* \* \* \*